Figure 1:
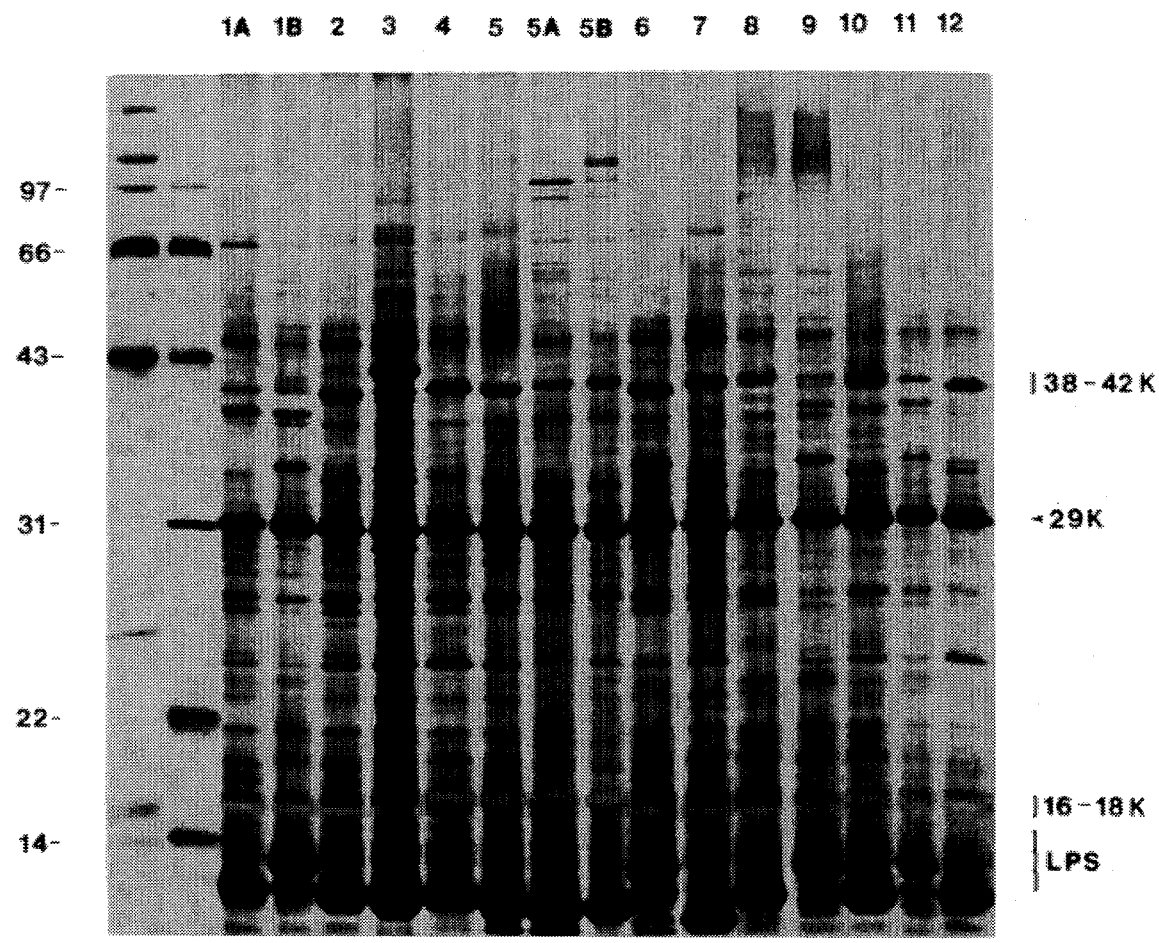

United States Patent [19]

Mulks et al.

[11] Patent Number: 5,543,304
[45] Date of Patent: Aug. 6, 1996

[54] 43 KD PROTEIN VACCINE AND METHOD FOR THE PRODUCTION THEREOF

[75] Inventors: Martha H. Mulks, Williamston; Brad J. Thacker, Bath; Maria W. T. Cruz, East Lansing, all of Mich.

[73] Assignee: Board of Trustees operating Michigan State University, East Lansing, Mich.

[21] Appl. No.: 227,259

[22] Filed: Apr. 14, 1994

Related U.S. Application Data

[62] Division of Ser. No. 920,869, Jul. 28, 1992.

[51] Int. Cl.$^6$ ............................ C12N 15/31; C12P 21/00; C12P 21/06
[52] U.S. Cl. .................... 435/69.3; 435/69.1; 435/172.3; 435/320.1; 424/200.1; 424/234.1
[58] Field of Search ................................ 435/69.3, 69.1, 435/172.3, 320.1; 530/350, 408, 825, 413; 424/92, 146.1, 164.1, 200.1, 234.1

[56] References Cited

U.S. PATENT DOCUMENTS 4,769,326  9/1988  Rutter ......................................... 435/68

FOREIGN PATENT DOCUMENTS

453024A1  of 0000  Germany.

OTHER PUBLICATIONS

Mulks, M., and Thacker, B., in Proc. Int. Pig Veter. Soc. 10 81 (1988).

P. J. Fedorka–Cray, M. J. Huether, D. L. Stine, and G. A. Anderson. Efficacy of a cell extract form Actinobacillus (Haemophilus) pleuropneumoniae Serotype 1 against disease in swine. Infect. Immun. 58:358–365 (1990).

J. Devenish, S. Rosendal, and J. T. Bosse. Humoral antibody response and protective Immunity in swine following immunization with the 104 Kildalton hemolysin of Actinobacillus pleuropneumoniae Infect. Immuno. 58:3829–3832 (1990).

D. K. Lenser, T. L. McDonald, and N. G. Miller. Veter. Micropbiol. 18:335–348 (1988).

Sanger, F., et al., PNAS 74:5463–5467 (1977).

Markmeyer, P., et al., Gene 93, 129–134 (1990).

Thwaits et al., Infection and Immunity, vol. 59, No. 2, Feb. 1991, pp. 544–549.

Young et al, Proc. Natl. Acad. Sci. USA, vol. 80, pp. 1194–1198, Mar. 1983.

Mulks et al, Abstracts of the 91st General Meeting of the American Society For Microbiology, 1991, D–230.

Mierendorf et al., Methods in Enzymology, vol. 152, 1987, pp. 458–469.

Uhlén et al, Methods in Enzymology, vol. 185, 1990, pp. 129–143.

Deneer et al, Vet. Inf. Dis. Org. Saskatoon, Saskatchewan, Canada, Microbial Pathogenesis, 1989, vol. 6, No. 6, pp. 425–432.

Primary Examiner—Mary E. Mosher
Assistant Examiner—Laurie Scheiner
Attorney, Agent, or Firm—Ian C. McLeod

[57] ABSTRACT

A protein derivable from Actinobacillus pleuropneumoniae (APP) having a molecular size ranging between 43 Kd on SDS PAGE is described. The protein is soluble on sodium lauryl sarcosinate (SLS) and not heat modifiable. The protein can also be derived by recombinant methods. The protein in a vaccine provides immunity against multiple serotypes of APP.

10 Claims, 5 Drawing Sheets

43 KD PROTEIN VACCINE AND METHOD FOR THE PRODUCTION THEREOF

This is a divisional of copending application Ser. No. 07/920,869 filed on Jul. 28, 1992.

BACKGROUND OF THE INVENTION

1. Field of the Invention

The present invention relates to a purified protein from *Actinobacillus pleuropneumoniae* (APP) outer membrane (OM) which is useful as a vaccine in swine. In particular, the present invention relates to a protein which has a molecular weight of about 43 Kd as measured by SDS PAGE, is not heat modifiable and is soluble in a 1% by weight to volume aqueous solution of sodium lauryl sarcosinate (SLS).

2. Prior Art

Most prior art relevant to bacterial vaccines is based upon killing a virulent strain of the bacteria by using formalin or by heat killing the bacteria. Generally the bacterial cells are a single serotype of the target bacteria. As a result, heterologous serotypes of the same bacteria can cause disease in spite of vaccination. The reason for this is not completely understood; however, it appears that antibodies to the heterologous serotype are not induced by the vaccine and thus there is no protective immunity.

With APP, there are multiple serotypes of the infecting organism. The serotypes are characterized based on antigenic differences in the capsular polysaccharides. Infection with one serotype provides protection against subsequent challenge with all serotypes. However, formalinized or heat-killed bacterins provide moderate protection against the homologous serotype and essentially no protection against heterologous serotypes. Research on antigens of APP and the immune response of swine to those antigens showed that there are a variety of antigenically similar outer membrane proteins that are found in all isolates of APP, regardless of serotype, which contribute to cross-protective immunity.

Mulks, M., and Thacker, B. in Proc. Int. Pig Veter. Soc. 10 81 (1988) describe an OM vaccine for pigs derived from *Haemophilus pleuropneumoniae* (now known as *Actinobacillus pleuropneumoniae* or APP). The vaccine contained APP outer membranes. The OM was produced by sonication of lysozyme-sucrose treated cells followed by sucrose density gradient centrifugation. The sonication was for 10–15 seconds. Lysozyme degrades peptidoglycan (the cell wall). Sucrose maintains the cell membranes remaining after treatment with the lysozyme until the cells are sonicated. No preservative was used in the preparation of the vaccine. Sucrose density gradient centrifugation and separation of OM is not a commercially viable method for producing the vaccine.

Other references for work on APP vaccines are:

(1) P. J. Fedorka-Cray, M. J. Huether, D. L. Stine, and G. A. Anderson. Efficacy of a cell extract form *Actinobacillus* (*Haemophilus*) *pleuropneumoniae* serotype 1 against disease in swine. Infect. Immun. 58:358–365 (1990). Two experimental APP vaccines were tested: (a) APP broth culture supernatant concentrated with 20% polyethylene glycol, containing primarily extracellular hemolysin; (b) OM prepared by a SLS extraction procedure. Both vaccines provided significant, although not complete, protection against homologous challenge as compared to unvaccinated controls.

(2) J. Devenish, S. Rosendal, and J. T. Bosse. Humoral antibody response and protective immunity in swine following immunization with the 104 kilodalton hemolysin of *Actinobacillus pleuropneumoniae*. Infect. Immun. 58:3829–3832 (1990). Purified 104 Kd hemolysin was tested as a vaccine, and elicited complete protection against mortality and significant, although far from complete, protection against lung involvement.

(3) D. K. Lenser, T. L. McDonald, and N. G. Miller. Protection of mice against the lethal effect of an intraperitoneal infection with *Haemophilus* (*Actinobacillus*) *pleuropneumoniae* after vaccination with capsular proteins. Veter. Microbiol. 18:335–348 (1988). The vaccines tested were: (a) whole cell bacterin; (b) capsular polysaccharide; (c) outer membranes prepared by a SLS extraction procedure; and (d) lipopolysaccharide (LPS) vaccines against APP in a mouse model. The results were: (a) whole cell bacterin gave some homologous but no heterologous protection; (b) capsular polysaccharide vaccine gave good homologous and no heterologous protection; (c) OM vaccine provided limited homologous and no heterologous protection; and (d) LPS vaccine provided no protection.

European Patent Application No. 453024A1 filed by vanden Bosch describes a vaccine prepared from a 42 Kd protein. This vaccine has 103/105 Kd hemolysin and 120 Kd cytotoxin and 42 Kd OMP. The protein described by this application is heat modifiable (30°–100° C. in buffer for 10 minutes) and sarcosyl insoluble and thus this protein is different from that of the present invention.

There is a need for an effective and reliable protein vaccine which does not require other APP cell components.

OBJECTS

It is therefore an object of the present invention to provide a novel protein vaccine which provides immunity to homologous and heterologous serotypes of a bacterium. Further, it is an object of the present invention to provide methods for producing the vaccine which are relatively easy to perform, safe and reliable. These and other objects will become increasingly apparent by reference to the following description and the drawings.

IN THE DRAWINGS

FIG. 1 is a sodium dodecyl sulfate polyacrylamide gel (SDS PAGE) of OM's prepared by the sucrose density gradient procedure from serotypes 1 to 12 of APP. Molecular size markers are in the far left lane. The important antigens are listed on the right side.

Figure 2:
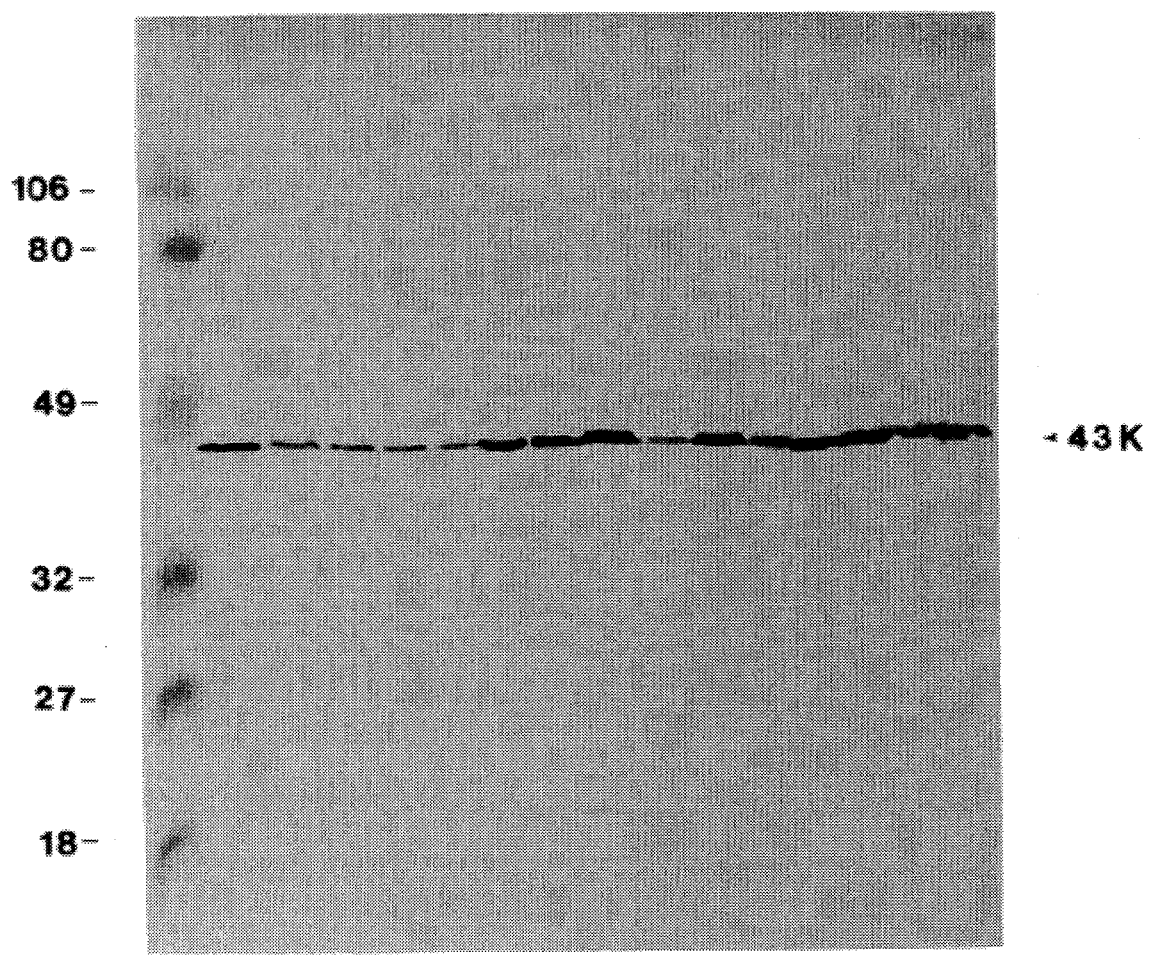

FIG. 2 is a Western blot (immunoblot) of OM's from APP serotypes 1 to 12 developed with MAb 3EH7 which is specific for the 43 Kd protein and HRP (horseradish peroxidase)-labeled goat antimouse immunoglobulin which complexes with the MAb.

Figure 3:
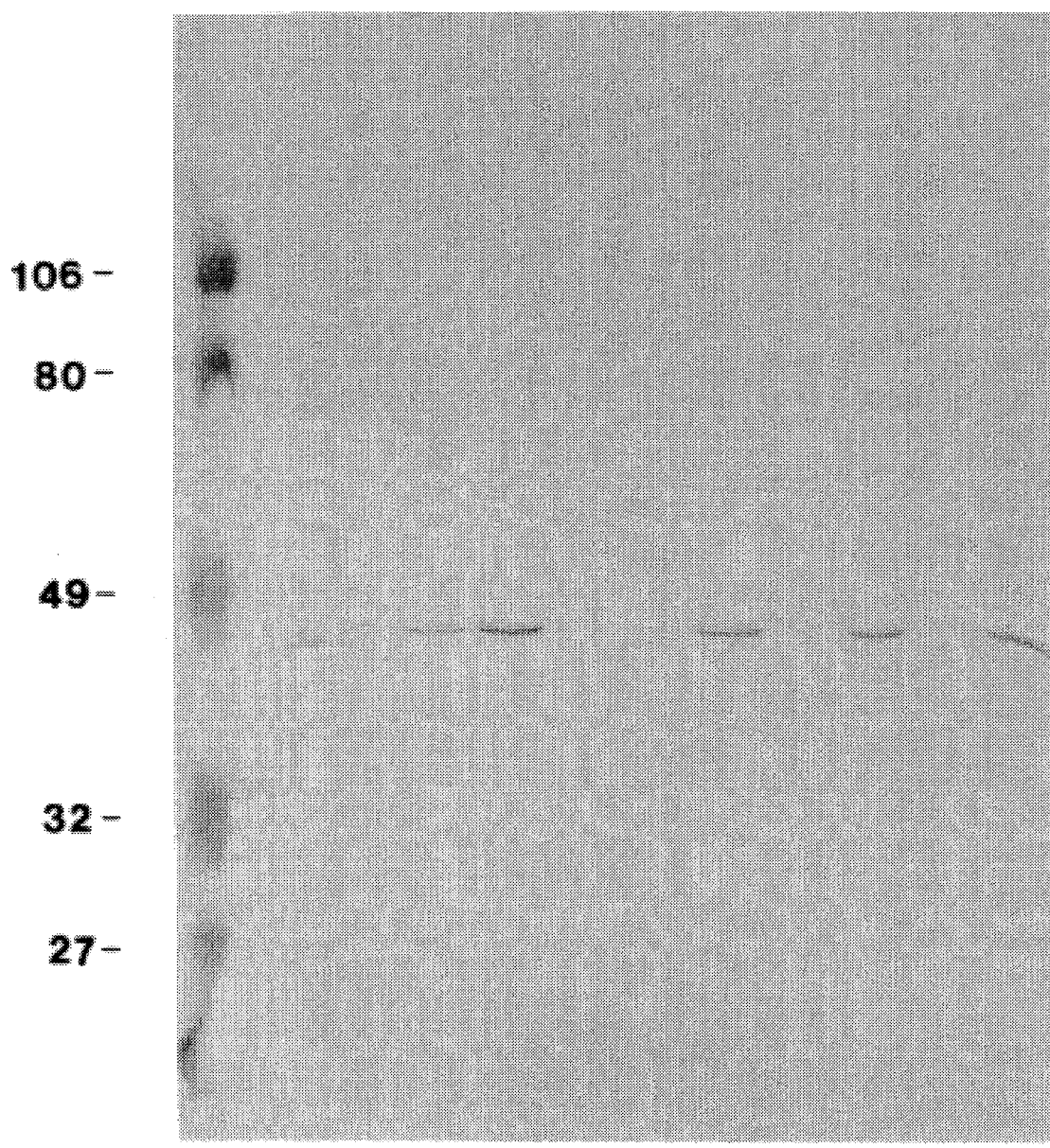

FIG. 3 is a Western blot of the λ-dash clones that tested positive in the primary screening with the pool of monoclonal antibodies. Five of the nine clones produced detectable 43 Kd antigen. Lane 1, pre-stained markers with the apparent molecular weights indicated; lane 2, *E. coli* LE392; lane 3, App serotype 5 OMP; lane 4, λEmbl 3; lanes 5–13, λ-dash clones.

Figure 4:
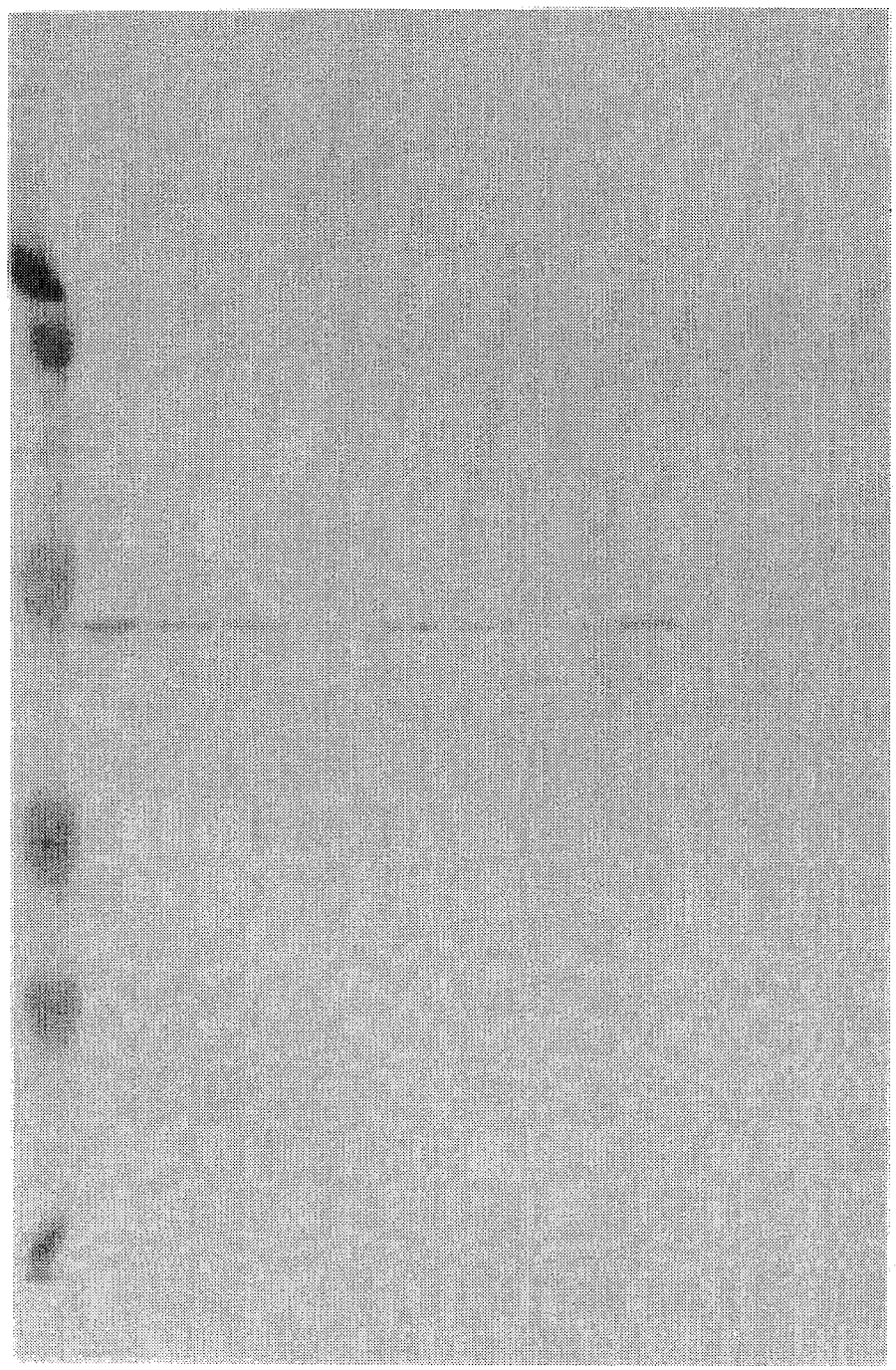

FIG. 4 is a Western blot of the λgt11 clones. Lane 1, pre-stained markers with the apparent molecular weights indicated; lane 2, App serotype 5 OMP; lanes 3–12, λgt11 clones.

Figure 5A:
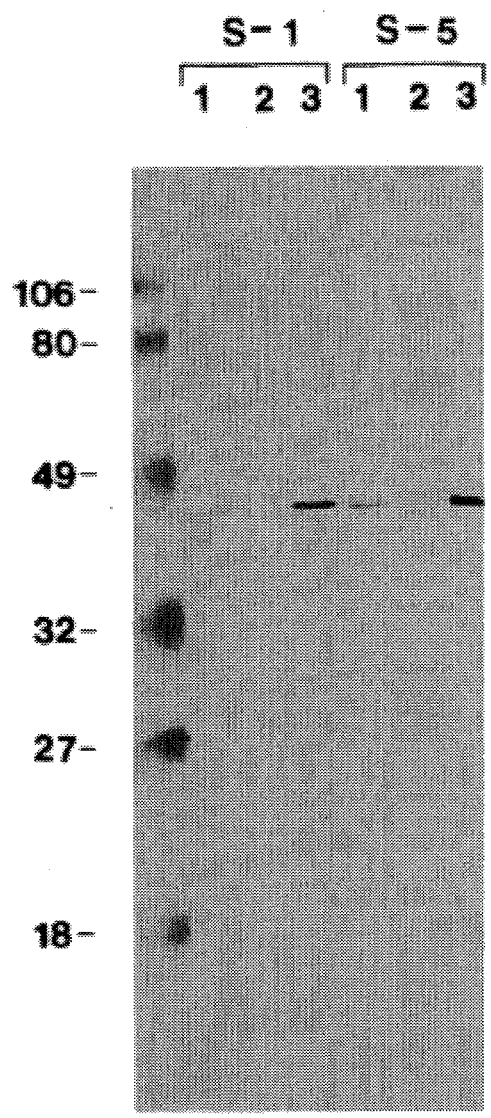

FIG. 5A is an immunoblot showing that the 43 Kd OMP is sarcosyl-soluble. Outer membranes from App serotypes 1 and 5 were prepared by a SLS extraction or a sucrose gradient procedure. Lanes 1, SLS-soluble OMPs; lanes 2, SLS-insoluble OMPs; lanes 3, OMPs prepared by the sucrose gradient procedure. The apparent molecular weights of the pre-stained markers are indicated.

Figure 5B:
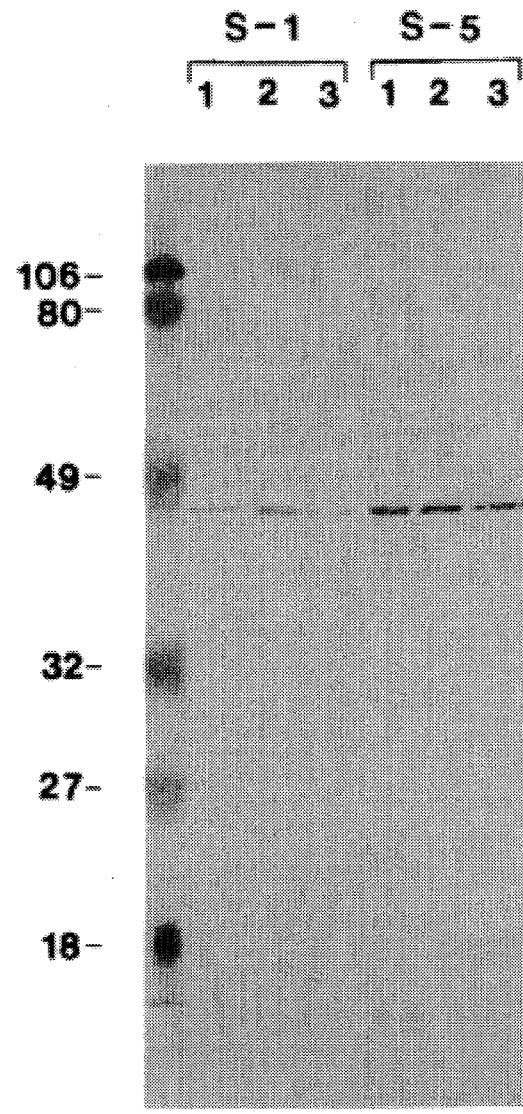

FIG. 5B is an immunoblot showing that the 43 Kd OMP from App serotypes 1 and 5 is not heat-modifiable. Samples in SDS-Sample buffer were heated for 10 minutes at (1) 37° C., (2) 50° C., and (3) 100° C. The apparent molecular weights of pre-stained standards are indicated.

GENERAL DESCRIPTION

The present invention relates to a protein derivable from an outer membrane of *Actinobacillus pleuropneumoniae* (APP) having a molecular size of 43 Kd as measured in SDS PAGE, which is not heat modifiable, and soluble in a 1% by weight to volume aqueous solution of sodium lauryl sarcosinate (SLS), wherein the protein is free of other proteins and antigens and the APP as intact cells, and to subunits of the protein which promote immunity to APP infection in swine. The protein is "not heat modifiable" when its apparent molecular weight is not changed by heat treatment at 30° C., 50° C. and 100° C.

The present invention also relates to a vaccine for the protection of swine against *Actinobacillus pleuropneumoniae* (APP) infection which comprises (a) a protein derivable from an outer membrane of APP having a molecular size of about 43 Kd as measured in SDS PAGE, not heat modifiable and soluble in a 1% by weight to volume aqueous solution of sodium lauryl sarcosianate (SLS), wherein the protein is free of other proteins, antigens and of the APP as intact cells, and (b) a carrier, and to subunits of the protein providing immunity from APP infection in the swine.

Further, the present invention relates to a method for vaccinating swine to provide protection against *Actinobacillus pleuropneumoniae* (APP) infection which comprises: injecting swine with a vaccine which is derivable from an outer membrane protein (OMP) of APP having a molecular size of about 43 Kd as measured in SDS PAGE, not heat modifiable and soluble in sodium lauryl sarcosianate (SLS), wherein the protein is free of other proteins, antigen and of the APP as intact cells, and to subunits of the protein providing immunity from APP infection in the swine.

The present invention also relates to an improved method for isolating a 43 Kd protein from outer membrane (OM) of *Actinobacillus pleuropneumoniae* (APP) by isolating cells of APP and separating the OM from the cells, which comprises: solubilizing the OM in an aqueous solution of sodium lauryl sarcosinate (SLS) to extract the 43 Kd protein from the OM; and isolating the 43 Kd protein from the solution. The SLS is used in an amount up to about 1% by weight to volume of solution. Preferably the 43 Kd protein is separated by affinity chromatography using column bound antibodies.

The present invention further relates to a method for producing a 43 Kd protein useful for protection of swine against Actinobacillus pleuropneumoniae APP infection derivable from an outer membrane derived protein of the APP having a molecular size of about 43 Kd as measured in SDS PAGE and soluble in sodium lauryl sarcosianate (SLS) and for producing subunits of the outer membrane protein providing immunity from infection by APP in the swine, wherein the protein is free of other proteins, antigens and of the APP as intact cells which comprises: providing DNA or an RNA encoding the protein or subunit of the protein in a vector which expresses the protein in a living cell; and producing the protein from the cell in an expression medium.

Finally the present invention relates to a fusion protein containing a non-toxic protein which allows purification of the fusion protein, an outer membrane protein of the APP having a molecular size of about 43 Kd as measured in SDS PAGE and soluble in 1% sodium lauryl sarcosianate (SLS) and subunits of the outer membrane protein providing immunity from infection by APP in the swine, wherein the protein is free of other proteins, antigens and the APP as intact cells.

The DNA encoding the 43 Kd protein is on deposit at the American Type Culture Collection (ATCC) in Rockville, Md. The deposit is phage λWC18 under the Budapest Treaty and has Access Number ATCC 75248.

In particular, the present invention relates to a method which comprises isolating a strain(s) of the APP from the swine host in a virulent form by passage of the strain(s) through the host; growing the isolated strain(s) in a growth medium; harvesting the strain(s) from the growth medium; preparing outer membranes by sucrose density gradient procedure; solubilizing the 43 Kd OMP; then separating it to produce the pure protein. The separation is particularly by affinity chromatography using monoclonal antibodies which are specific for the 43 Kd protein bound to a column, although other methods can be used. A molecular sieve can be used. The proteins are also produced by recombinant methods by isolating the DNA encoding the protein(s).

As indicated earlier, there are 12 serotypes of APP, based on antigenic differences in the capsular polysaccharide, although only serotypes 1, 3, 5, and 7 are important in the United States. Virulence factors include the capsule, lipopolysaccharide (LPS), hemolysins and cytolysin, and outer membrane proteins. The capsular polysaccharide, which is the primary serotype-specific antigen, does not alone cause lesions but is believed to protect the organism from respiratory defense mechanisms. Antibody against capsular material confers at least some serotype-specific protection against APP disease. LPS, also known as endotoxin, is responsible for many of the acute pulmonary lesions. Antibodies to LPS may be partially cross-reactive with LPS from other serotypes; e.g., antibodies to serotype 7 LPS cross-react strongly with serotype 4 LPS, but not with LPS from other serotypes, and antibodies to LPS from serotypes 2, 3, and 5 cross-react. However, LPS-specific antibodies seem to provide only a partial and short-term immunity against APP infection. Hemolysins and cytolysin are cytocidal to red blood cells, pulmonary macrophages, and neutrophils, and also interfere with their phagocytic function. These toxins are responsible for much of the hemorrhage and tissue necrosis that is a hallmark of APP disease. Specific antibody against these exotoxins, while not preventing infection, does greatly reduce the severity of the disease.

As indicated earlier, natural and experimental infection with one APP serotype generally provides protection against subsequent infection with other serotypes. However, current killed whole cell vaccines, which elicit mainly antibody to surface exposed antigens, especially capsular polysaccharides, provide only partial protection against infection with the APP serotype(s) used in the vaccine, and no cross-protection against other serotypes. These data suggest the existence of common sub-capsular antigens that confer cross protective immunity and that are exposed during infection but not vaccination. Research has provided information about the antigenic structure of the APP cell surface. It has been shown that isolates of all 12 APP serotypes contain several common outer membrane proteins (OMP), including a 16–18 Kd protein found in many species of gram-negative bacteria, a 29/41 Kd heat-modifiable protein, a major protein of 38–42 Kd, and a 43 Kd protein. Western blot analysis has demonstrated that convalescent sera from APP infected pigs contains antibodies against these as well as several other common OMPs. An outer membrane vaccine from APP serotype 5 (APP-5) has been produced as shown in Table 1, which contains OMP's, capsular polysaccharide, and LPS, and it has been found that this vaccine provides excellent protection against infection with both the homologous and heterologous serotypes, demonstrating that cross-protective immunity can be achieved if the subcapsular antigens are properly exposed.

TABLE 1

Protection against APP Challenge Provided by OM Vaccine

| Vaccine | Challenge | No. Pigs | % Mortality | % Pneumonia |
| --- | --- | --- | --- | --- |
| Control | APP-5 | 5 | 3/5 | 43.0 |
| OMP-5 | APP-5 | 5 | 0/5 | 1.0 |
| Control | APP-1 | 4 | 2/4 | 53.0 |
| OMP-5 | APP-1 | 5 | 0/5 | 11.8 |
| Commercial | APP-1 | 4 | 0/4 | 11.4 |

However, production of such an outer membrane vaccine would be too expensive to be commercially feasible and the contents of the vaccine from lot to lot would be variable.

A common outer membrane protein found in all serotypes of APP has been identified that can be used as a purified protein vaccine against disease caused by this organism. This protein has an apparent molecular weight of 43 Kd, as determined by sodium dodecyl sulfate polyacrylamide gel electrophoresis (SDS-PAGE). FIG. 1 shows the size of the protein. This protein is found in all isolates of APP, regardless of serotype, and is immunogenic in swine infected with APP. This protein is readily detectable in APP outer membranes prepared by the sucrose density gradient procedure that separates outer from cytoplasmic membranes by differences in buoyant density. It is not detectable in outer membranes prepared by SLS treatment of a total APP membrane fraction, since it is soluble in SLS and the fraction considered to be outer membrane is the SLS insoluble fraction. The protein is also not heat-modifiable.

Monoclonal antibodies (MAbs) have been produced against this common 43 Kd protein. All of these MAbs cross-react with a similar protein in isolates of all other APP serotypes, and several of these MAbs have bacteriocidal activity against APP. These monoclonal antibodies do not cross-react with outer membranes of other related gram-negative microorganisms. Because this 43 Kd protein is a common antigen in all APP serotypes, is immunogenic in infected swine, and is a target for bacteriocidal activity, this protein is useful for a recombinant or purified protein vaccine. FIG. 2 and Table 2 show the results with the antibody.

TABLE 2

Bacteriocidal Activity of MABs Developed against the 43 Kd OMP from APP-5 vs. APP serotypes

| MAb | APP-1 | APP-2 | APP-4 | APP-5 | APP-6 | APP-7 |
| --- | --- | --- | --- | --- | --- | --- |
| 1 | − | − | − | + | − | − |
| 2 | + | + | + | + | + | − |
| 3 | + | − | − | + | + | − |
| 4 | + | + | + | + | + | − |

The gene for the 43 Kd protein has been cloned using monoclonal antibodies against this protein to identify clones of APP genomic DNA in a lambda vector which express this antigen. Once identified, the gene for the 43 Kd protein can be subcloned into a high yield expression vector to permit production of large amounts of the 43 Kd protein, which can then be purified by affinity chromatography using the monoclonal antibodies.

An alternative procedure to produce the pure 43 Kd protein for the vaccine is to purify the protein from APP outer membranes. A purification scheme is: 1) preparation of APP-5 outer membranes by sucrose density gradient centrifugation and precipitation of the SLS insoluble fraction; 2) separation of the soluble fraction; and 3) affinity purification of the solubilized 43 Kd protein using monoclonal antibodies.

Preferably the vaccine contains between about 0.001 and 10 mg of protein per ml. This provides sufficient protein for vaccination and for providing immunity to APP.

A sterile carrier or adjuvant is used in the vaccine. The preferred carrier is water or an aqueous saline or phosphate buffer saline (PBS) solution. The preferred adjuvant for the vaccine is "EMULSIGEN" (MVP Labs, Ralston, Neb.), which is a paraffin oil in water emulsion, since it can be used in food animals. Freund's Incomplete Adjuvant, which is 15 percent by weight mannide monooleate and 85% paraffin oil, available from Difco, Detroit, Mich. can be used in non-food (i.e. laboratory animals). The adjuvants aid in slowly releasing the vaccine into the animal and in potentiating the immune response. Any commercial oil emulsion adjuvants can be used, but not aluminum hydroxide.

SPECIFIC DESCRIPTION

Experimental Protocols and Results

EXAMPLE 1

Identification and characterization of major sub-capsular surface antigens of A. pleuropneumoniae:

To identify cross-reactive surface antigens of A. pleuropneumoniae, outer membranes of APP were examined by SDS-PAGE and Western blot analysis. Outer membranes were prepared from type strains of serotypes 1–12 and from field isolates of serotypes 1, 5, and 7 by isopycnic sucrose density centrifugation. Bacteria were grown overnight at 37° C. in Brain Heart Infusion broth containing 10 µg/ml nicotinamide adenine dinucleotide (AND). Bacteria were harvested by centrifugation, washed in buffer, and spheroplasted by treatment with lysozyme-sucrose-EDTA. Spheroplasts were ruptured by sonication on ice, and the membrane fraction pelleted by ultracentrifugation. The membrane pellet was resuspended in buffer and outer and cytoplasmic membranes separated by ultracentrifugation over a sucrose density step gradient.

Components of the outer membranes, including proteins, lipopolysaccharide, and capsular polysaccharides, were separated by sodium-dodecylsulfate polyacrylamide gel electrophoresis (SDS-PAGE), and the gels stained with a differential Coomassie blue-silver stain (FIG. 1). Several classes of antigens were present in similar forms, with minor variations in molecular weight, in all the isolates examined, regardless of serotype. These included major proteins with estimated molecular weights of 16–18K, 29K, 38–42K, 41K, 43K, 66K and 97K. Also identified were LPS and capsular polysaccharide components of the outer membrane, including rough type LPS (12–14K apparent molecular weight on SDS-PAGE) in all serotypes and laddered smooth type LPS in serotypes 4 and 7, and high molecular weight capsular polysaccharide in all serotypes. We found some variation in outer membrane protein and LPS profiles between serotypes, but in general little variation among isolates of the same serotype.

EXAMPLE 2

Evaluation of the immune response of swine to the 43 Kd protein of *A. pleuropneumoniae*:

Sera from swine were collected from chronically infected herds; from animals experimentally infected with serotypes 1, 3, 5, and 7; and from animals vaccinated with several different vaccine preparations (including whole cell bacterins, sonicated whole cell, and outer membrane vaccines), as well as from uninfected control animals, and have evaluated the immune responses of these animals to capsular antigens and to outer membrane protein and LPS antigens of APP. Western blot analysis was used to show that both naturally and experimentally infected pigs develop an antibody response to the common 43 Kd outer membrane protein, as well as to several other OMPs, LPS, and capsular polysaccharide. Swine vaccinated with the outer membrane vaccine also develop a strong immune response to this protein.

The procedure used for Western blot analysis is as follows: outer membrane preparations, TCA-precipitated cell culture supernatants containing hemolysins, purified proteins, purified LPS, or other antigens separated by standard SDS-PAGE or by modifications designed for improved resolution of LPS are electrophoretically transferred to nitrocellulose membranes using a BioRad Transblot cell. Blots are blocked with PBS+1% BSA+0.05% Tween 20 and incubated overnight with antisera to allow antigen-antibody complexes to ferm. After washing with PBS-Tween, the blots are developed with either $I^{125}$-Labelled Protein A, which can detect most porcine immunoglobulins, or with rabbit anti-porcine IgG, IgM or IgA (commercially available from multiple sources), followed by $I^{125}$-labelled anti-rabbit immunoglobulin. Blots with mouse monoclonal antibodies (MAb) as the primary antiserum are developed with either $I^{125}$-labelled anti-mouse IgG+IgM, or with horseradish peroxidase tagged anti-mouse immunoglobulin and 4-chloronaphthol as the colorimetric substrate.

EXAMPLE 3

Development of monoclonal antibodies against *A. pleuropneumoniae*:

Monoclonal antibodies were produced against the 43 Kd OMP of APP, using the following procedures. Balb/C mice were immunized intraperitoneally with either whole killed cells of APP or with outer membranes prepared by sucrose density gradient centrifugation. Mice received a single antigen boost 4 weeks later and were sacrificed 3 days after the boost. Immune spleen cells were fused with P3-NSi-1 (NS-1) mouse myeloma cells in 50% polyethylene glycol 1500, and NS-1:spleen cell hybrids selected by culturing in hypoxanthine-aminopterin-thymidine medium. Cell cultures were screened for production of relevant antibodies by ELISA against APP outer membranes. The preferred monoclonal was 3EH7 which is deposited at Michigan State University, East Lansing, Mich. Positive clones were subcloned by limiting dilution to ensure that each clone included only a single MAb producing cell line. Positive clones were expanded to allow production of sufficient antibody for further screening and isotyping. Reactions with specific OMPs or other OM antigens were determined by Western blot. Several of the MAbs produced in these fusions have been directed against the 43 Kd OMP. Western blots of APP outer membranes developed with these monoclonal antibodies confirm that there are antigenically similar proteins in all serotypes of APP (FIG. 2).

EXAMPLE 4

Assay of bactericidal activity of monoclonal antibodies against APP.

These assays demonstrate that monoclonal antibodies against the 43 Kd common OMP trigger complement mediated killing of APP cells (Table 2).

1. Bacteria:
   a. Grow bacteria either in broth to mid-to-late log phase or on plates (16–18 hour culture)
   b. Wash bacterial cells once with Hanks Buffered Salts Solution (HBSS).
   c. Suspend bacteria in sterile HBSS to a concentration of $3\times10^8$/ml (OD520=0.3–0.4).
   d. Store bacterial suspension on ice for no more than 15–20 minutes before use.
   e. Dilute bacterial suspension 1:7000 just before use.
2. Antiserum:
   a. Heat inactivate to denature complement, 30 minutes at 56° C.
   b. Dilute in sterile HBSS, in serial two-fold dilutions.
3. Complement:
   a. Use pre-immune rabbit serum as a complement source.
   b. Absorb the serum against the bacteria to be tested for 1 hour at 4° C.—to do this, mix 1 ml serum with 1 ml bacteria ($10^{10}$ per ml), let stand 1 hour at 4° C., then centrifuge out bacteria and retain supernatant=absorbed serum.
   c. Filter sterilize the absorbed serum.
   d. Heat inactivate an aliquot, as a control (30 minutes at 56° C.).
   e. It may be necessary to dilute complement in HBSS, 1:2 or even 1:10, if the complement source control shows significant bactericidal activity of its own.
4. Assay procedure:
   a. Mix 50 µl bacterial suspension
      +100 µl HBSS
      +50 µl complement
      +50 µl diluted antiserum
   b. Incubate mixture at 37° C. in a water bath shaker for varying times (usually 0, 30, 60, 90 and 120 minutes).

c. At each time point: remove sample from water bath; vortex to mix thoroughly; plate 25 µl, in triplicate.

d. Incubate plates overnight at 37° C. Count colonies from each plating, and average the three counts to determine average colony count per sample.

e. Compare experimental samples to controls to determine % killing due to bactericidal activity of serum.

EXAMPLE 5

Cloning of the gene for the 43 Kd OMP.

An APP lambda-dash library (provided by Dr. Douglas K. Struck of Texas A & M University) was screened immunologically using a pool of monoclonal antibodies (MAb) against the 43 Kd outer membrane protein. *E. coli* Y1090 was infected with the phage and plated to give a density of 500 plaques per plate. The plates were incubated overnight at 37° C. Plaques were lifted off the plates using nitrocellulose filters. The filters were blocked with 5% skim milk and incubated with the pool of Mabs overnight at room temperature. After washing with PBS-Tween 20, the filters were incubated for 2 hours with HRP-labelled anti-mouse IgG and IgM. The antigen-antibody complexes on the filters were detected using 4-chloro-1-naphthol, a colorimetric substrate for HRP. Of the 5000 plaques screened, 9 were positive by this test, indicating that these phage produced the 43 Kd antigen recognized by the MAbs.

Positive phage were transferred to a fresh bacterial lawn and plaques were again lifted and tested immunologically for the 43 Kd protein. All 9 clones were positive.

Plate lysates of the 9 positive clones were tested for the 43 Kd antigen by Western blot. An aliquot of the plate lysate was precipitated with an equal volume of 20% cold trichloroacetic acid. The precipitate was washed with methanol and boiled in SDS-sample buffer for 5 minutes. Samples were separated on a 10% SDS-PAGE gel and then electroblotted onto a nitrocellulose filter. After blocking with 5% skim milk, the filter was incubated overnight with pooled MAbs. After washing, the filter was incubated for 2 hours with the HRP-labelled anti-mouse antibody. The HRP color reagent was used to identify the 43 Kd antigen. Of the 9 clones that had tested positive in the plaque lift assays, 5 produced a 43 Kd protein as detected by Western blot (FIG. 3).

EXAMPLE 6

Large scale preparations of recombinant phage were prepared by plate lysates. Phage particles were precipitated from RNase/DNase treated plate lysates using polyethylene glycol/NaCl. After releasing the DNA from the phage particles via SDS treatment, the DNA was purified by passage over a QIAGEN column. The DNA was analyzed with restriction enzymes; the 5 positive clones had inserts ranging from 14 to 20 kb. One phage, which has an insert of ~16 Kb, is deposited as λWC18 ATCC No. 75248.

A SalI fragment, representing the intact insert (~16 kb) from λWC18, was isolated and digested with EcoRI. This digestion yielded 4 DNA fragments, of 2.3, 3.5, 4.0 and 6.2 kb. The entire digestion mixture was ligated with EcoRI-cut lambda gt11 arms. The mixture was then packaged and the lambda gt11 clones screened immunologically with pooled MAbs. Several positive clones were identified. Of the 10 that were picked and tested for the production of the 43 Kd protein, 9 produced detectable antigen on Western blot (FIG. 4).

These phage clones are expanded, and the inserts mapped with restriction enzymes. Pieces of the inserts are subcloned into expression vectors to facilitate further identification and characterization of the 43 Kd protein. Using the MAb pool to screen immunologically for production of this protein, subclones can be identified which produce the intact 43 Kd protein. These recombinant plasmids can be mapped by restriction enzyme digestion and deletion analysis. Once the approximate limits of the gene have been established, the gene will be subcloned into M13mp18 or 19, nested deletions constructed, and the nucleotide sequence determined by the dideoxy chain termination method of Sanger (Sanger, F., et al., PNAS 74:5463–5467 (1977)).

An alternative procedure to produce sufficient pure 43 Kd protein for vaccine studies is to purify the protein from APP outer membranes. A potential procedure includes: 1) preparation of APP-5 outer membranes by sucrose density gradient centrifugation; 2) solubilization of the 43 Kd protein with 1% sarkosyl; and 3) affinity purification of solubilized 43 Kd protein using monoclonal antibodies.

EXAMPLE 7

Characterization of the 43 Kd OMP

FIG. 5A: demonstrates that the 43 Kd protein is soluble in 1% sarkosyl.

FIG. 5B: demonstrates that the 43 Kd protein is not heat modifiable.

EXAMPLE 8

Production of 43 Kd protein in *E. coli* expression vectors

The gene for the 43 Kd protein is subcloned into a high yield expression vector, such as the pAX fusion protein vectors in *E. coli* (Markmeyer, P, et al., Gene 93, 129–134 (1990)), to permit production and purification of substantial amounts of the cloned protein for use in the proposed vaccine studies. If the pAX vectors are used, for example, the expressed fusion protein consists of β-galactosidase (a non-toxic protein), a collagen fragment which acts as a hinge region to separate β-gal from the cloned protein, an endoproteinase Xa recognition site, and the cloned protein of interest. IPTG (isopropyl-β-D-thiogalactopyranoside) is used for expression of the fusion protein. Fusion proteins can be purified by affinity chromatography over an immobilized APTG (para-aminophenyl-β-D-thiogalactopyranoside) column (APTG is a substrate which binds to, but is not degraded, by β-gal). IPTG can also be used on the column. The purified fusion protein is then cleaved by endoproteinase Xa to release the cloned protein from the β-gal moiety. The cloned protein can be purified on an antibody affinity column. Urease or staphylococcal protein A can be expressed in place of β-gal as is known in the prior art. Similar systems can be used for other expression vectors.

EXAMPLE 8

The 43 Kd protein is injected into the swine subcutaneously, using a dosage of 0.1 to 10 mg of protein per dose of vaccine. The vaccine contains 25% Emulsigen as an adjuvant and is injected at a dosage of 0.0001 to 1 mg of protein per kg of swine body weight. Immunity can be achieved by this method.

It is intended that the foregoing description be only illustrative of the present invention and that the present invention be limited only by the hereinafter appended claims.

We claim:

1. A method for producing a 43 Kd protein useful for production of antibodies in swine against *Actinobacillus pleuropneumoniae* (APP) infection derivable from an outer membrane derived protein of the APP having a molecular size of about 43 Kd as measured in SDS PAGE and soluble in 1% sodium lauryl sarcosinate (SLS) and for producing subunits of the outer membrane protein providing immunity from infection by APP in the swine, wherein the protein is free of other proteins and antigens and of the APP as intact cells which comprises:

(a) providing DNA encoding a fusion protein which includes the 43 Kd protein and a non-toxic protein in a vector which expresses the protein in a living cell, wherein the 43 Kd protein is produced by the DNA contained in λWC18 deposited as ATCC 75248;

(b) producing the fusion protein from the cell in an expression medium, (c) isolating the fusion protein by binding using affinity chromatography using the nontoxic protein for the binding; and (d) separating the 43 Kd protein from the fusion protein.

2. The method of claim 1 wherein the fusion protein contains a collagen fragment and wherein the collagen fragment separates the non-toxic protein and the protein.

3. The method of claim 2 wherein a column containing sites which bind the non-toxic protein by the affinity chromatography is used to purify the fusion protein by binding only the fusion protein.

4. The method of claim 3 wherein the sites contain para-aminophenyl-β-D-thiogalactopyranoside immobilized on the column and the non-toxic protein is beta-galactosidase.

5. The method of claim 1 wherein the fusion protein is produced and is purified by a column.

6. The method of claim 1 wherein the nontoxic protein is selected from the group consisting of beta-galactosidase, urease and staphylococcal protein A.

7. The method of claim 1 wherein the nontoxic protein is beta-galactosidase.

8. The method of claim 1 wherein the expression medium contains isopropyl-β-D-thiogalactopyranoside.

9. The method of claim 1 wherein a SalI fragment of λWC18 is used to provide the DNA.

10. The method of claim 1 wherein the vector is pAX in *E. coli.*

* * * * *